United States Patent [19]

Stevenson et al.

[11] Patent Number: 4,623,716

[45] Date of Patent: Nov. 18, 1986

[54] PROCESS FOR THE PREPARATION AND PURIFICATION OF PEPTIDES

[75] Inventors: David Stevenson, Scarsdale, N.Y.; Mohammad A. Islam, Edison, N.J.

[73] Assignee: USV Pharmaceutical Corp., Ft. Washington, Pa.

[21] Appl. No.: 667,025

[22] Filed: Nov. 1, 1984

[51] Int. Cl.$^4$ .................................................. C07K 1/00
[52] U.S. Cl. ..................................... 530/333; 530/307; 530/311
[58] Field of Search ................. 260/112.5 T; 530/333, 530/307, 311

[56] References Cited

U.S. PATENT DOCUMENTS

| | | | |
|---|---|---|---|
| 3,929,758 | 12/1975 | Hughes et al. | 260/112.5 S |
| 4,033,940 | 7/1977 | Hughes et al. | 260/112.5 T |
| 4,212,795 | 7/1980 | Hughes et al. | 260/112.5 T |

Primary Examiner—Delbert R. Phillips

[57] ABSTRACT

Peptides, such as calcitonin, having two cysteine residues connected by a disulfide bond are prepared by a process which includes the step of cyclizing the cysteines at a pH of 8.5 to 9.0, and a concentration of 0.4 to 1.8 mg of peptide per ml of solution. These novel conditions produce rapid cyclization with an unforeseen improvement in yield.

4 Claims, No Drawings

PROCESS FOR THE PREPARATION AND PURIFICATION OF PEPTIDES

FIELD OF THE INVENTION

This invention relates to the preparation of biologically active peptides, including calcitonins, somatostatin, vasopressin, and oxytocin. It includes a new set of process conditions, and an intermediate isolated from process solutions.

BACKGROUND OF THE INVENTION

The present invention relates generally to cyclization of peptides. More particularly, the present invention relates to methods for treating peptides containing an even number of cysteine groups to produce a disulfide bond between pairs of such groups and to form a ring structure. The method of the invention is useful in the synthesis of peptides which have biological activity and which have therapeutic value in the treatment of certain diseases in animals and man.

Many peptides which contain a disulfide ring are known which are biologically active and are useful in the treatment of diseases. Somatostatin, which is described in U.S. Pat. No. 3,904,594 to Guillemin et al, has been shown to be effective in the inhibition of growth hormone by the pituitary gland. Somatostatin has been proposed for use in the treatment of acromegaly and diabetes. Somatostatin contains a disulfide bond between the cysteine residues in positions 3 and 14 in its amino acid sequence. Vasopressin and its analog lypressin are used as antidiuretic drugs in man. These peptides contain a disulfide bridge structure between cysteine groups at positions 1 and 6 in their amino aicd sequences. Oxytocin is used for the induction or stimulation of labor in humans, in animals and also to control postpartum uterine bleeding. Oxytocin contains a disulfide bridge structure between the cysteine groups at positions 1 and 6 in its amino acid chain. Calcitonins contain a ring structure involving cysteine groups at the first and seventh positions in their amino acid chain. Calcitonins are useful in the treatment of Paget's disease.

The amino acid sequences of the above described biologically active peptides containing cysteine groups joined by a disulfide bond in a ring structure are set forth in Table 1, herein below:

TABLE 1

Somatostatin:
H—Ala—Gly—

—Cys—Lys—Asn—Phe—Trp—Lys—Thr—Phe—Thr—Ser—Cys—

—OH

Vasopressin:

H—Cys—Tyr—Phe—Gln—Asn—Cys—Pro—Arg—Gly—NH$_2$

Oxytocin:

H—Cys—Tyr—Ile—Gln—Asn—Cys—Pro—Leu—Gly—NH$_2$

Human Calcitonin:

H—Cys—Gly—Asn—Leu—Ser—Thr—Cys—Met—Leu—

TABLE 1-continued

—Gly—Thr—Tyr—Thr—Gln—Asp—Phe—Asn—Lys—Phe—

—His—Thr—Phe—Pro—Gln—Thr—Ala—Ile—Gly—Val—

—Gly—Ala—Pro—NH$_2$

Porcine Calcitonin:

H—Cys—Ser—Asn—Leu—Ser—Thr—Cys—Val—Leu—

—Ser—Ala—Tyr—Trp—Arg—Asn—Leu—Asn—Asn—Phe—

—His—Arg—Phe—Ser—Gly—Met—Gly—Phe—Gly—Pro—

—Glu—Thr—Pro—NH$_2$

Bovine Calcitonin:

H—Cys—Ser—Asn—Leu—Ser—Thr—Cys—Val—Leu—

—Ser—Ala—Tyr—Trp—Lys—Asp—Leu—Asn—Asn—Tyr—

—His—Arg—Phe—Ser—Gly—Met—Gly—Phe—Gly—Pro—

—Glu—Thr—Pro—NH$_2$

Salmon Calcitonin:

H—Cys—Ser—Asn—Leu—Ser—Thr—Cys—Val—Leu—
   1    2    3    4    5    6    7    8    9

—Gly—Lys—Leu—Ser—Gln—Glu—Leu—His—Lys—Leu—
  10   11   12   13   14   15   16   17   18   19

—Gln—Thr—Tyr—Pro—Arg—Thr—Asn—Thr—Gly—Ser—
  20   21   22   23   24   25   26   27   28   29

—Gly—Thr—Pro—NH$_2$
  30   31   32

Eel calcitonin has the structure of salmon calcitonin except for having Asp in position 26, Val in position 27, and Ala in position 29.

The present invention is also applicable to the numerous calcitonin analogs known in the art, in which one or more of the amino acids of the naturally occurring sequence are modified or deleted, or one or more acids are added, with the retention or even enhancement of biological activity.

In U.S. Pat. Nos. 3,926,938, 4,062,815, 3,929,758, 4,033,940, 4,336,187, 4,388,235 and 4,391,747 are disclosed improved syntheses of calcitonins including the salmon calcitonin referred to above.

DESCRIPTION OF THE PRIOR ART

It is known how to prepare synthetically a peptide having a closed disulfide ring structure namely by forming the noncyclic peptide having the desired amino acid sequence and then subjecting the peptide to an oxidative process using oxidizing agents to form the disulfide bond between two cysteine residues. One oxidative process for producing peptides having a disulfide bond between two cysteine residues is described in the literature, Hope E. D., Murti B. X. and du Vigneaud V., J. Biol. Chem., V.237, page 1563 (1962). This method is commonly referred to as the du Vigneaud Method. In the du Vigneaud Method, a buffered solution of the linear peptide containing at least a pair of cysteine groups is oxidized by adding a buffered solution of a ferricyanide salt to the peptide solution at a constant pH.

A main disadvantage of the du Vigneaud Method and other oxidative processes is the exposure of the highly reactive peptide molecule to oxidizing agents, which risks causing cross linking and polymerization of the peptide molecules to occur. The known oxidative methods for forming a closed disulfide ring structure can cause inactivation of the peptide and a lower yield of biologically active peptide product.

U.S. Pat. No. 3,929,758 to Hughes et al, describes a further method for the synthesis of disulfide cyclic peptides. In the method of the Hughes '758 patent a disulfide cyclic peptide is prepared by first preparing a peptide containing at least two cysteine moieties one of which is protected by an n-alkylthio group. Thereafter the protected peptide is subjected to a procedure in which the peptide is held in solution substantially free of oxygen at a pH of 5 to 10 until rearrangement takes place to yield a cyclic disulfide peptide. During the rearrangement the n-alkylthio group is displaced from the amino acid chain. This disclosure does not suggest the particular combination of conditions of the present invention. The method is also more time consuming than the simple oxidative methods which have been heretofore used, and it calls for the peptide to be relatively highly diluted.

According to U.S. Pat. No. 4,216,141, peptides containing a disulfide bond between two cysteine residues are formed by a procedure that does not require the formation of intermediates prior to forming the disulfide bond. The process involves a simple oxidation of a peptide containing at least two cysteine moieties. The oxidation step is accomplished under conditions whereby the sulfhydryl concentration in a reaction mixture is maintained at substantially zero during the reaction. The process involves the formation of an acidified aqueous solution of a peptide containing at least one pair of cysteine moieties. Thereafter, the acidic peptide solution is added incrementally to a buffered solution containing an oxidizing agent. The period between addition of the increments of acidic peptide solution is such that the oxidizing reaction to form the disulfide bond occurs substantially instantaneously and the increments are of such size that the sulfhydryl concentration during the reaction remains substantially constant and at a level of substantially zero equivalent to infinite dilution.

U.S. Pat. No. 4,212,795 discloses that a peptide containing a structure having two cysteine residues participating in external disulfide bonds with protecting groups may be held in solution (any solution in which it is soluble), with aqueous or alcoholic solutions preferred, at a preferred pH of from about 5 to 10 in the absence of oxygen and oxidizing substances until the external disulfide bonds undergo spontaneous rearrangement to the desired internal disulfide peptide with the displacement of a non-peptide disulfide by-product. The rate of the rearrangement reaction is said to be facilitated by the presence (in amounts of 0.01 molar equivalents per mole of peptide) of a free thiol compound, such as aliphatic or aromatic thiols, the amino acid cysteine or thioglycolic acid or its derivatives. The patent states that the rate of rearrangement is also facilitated by adjusting the pH of the solution to from 5.0 to 8.5, preferably from 6.0 to 8.5, and better at about 7.5, as by the addition of ammonium or alkali hydroxides to the solution. According to the patent, pH below 6.0 may be used, but the rearrangement proceeds more slowly than is desirable, and a pH up to about 10.0 or 10.5 can be used, but when a pH higher than about 9.0 is used, there is some danger of loss in yield.

SUMMARY OF THE INVENTION

The invention comprises a process for forming a disulfide bridge in a peptide containing at least one pair of cysteine moieties. It involves adjusting the pH of a solution of the peptide in its uncyclized form, to a value of 8.5 to 9.0, and a concentration of about 0.4 to 1.8 mg of peptide per ml of solution, and holding the solution at those conditions until the bridge forms.

DESCRIPTION OF INVENTION

The process of the invention is applicable to the synthesis of any cyclic disulfide peptide where the disulfide bond is between at least one pair of cysteine residues in the amino acid chain. The process is particularly suitable for the synthesis of labile, biologically active peptides because the disulfide bond is formed under conditions which avoid cross linking and polymerization of the peptide and do not otherwise disturb peptide structure.

Resin Peptide Synthesis

The process of the invention starts with the preparation of the peptide by building the amino acid chain sequence of any peptide containing at least two cysteine residues. The amino acid chain sequence may be assembled by use of classical synthesis techniques or by solid phase techniques.

Preferably, the peptide is assembled using solid phase synthesis. One can start with a resin called benzhydryl amine resin (BHA resin). This resin is derived from a cross-linked polystyrene bead resin manufactured by copolymerization of styrene and divinylbenzene. Resin of this type is known and its preparation is further demonstrated by Pietta et al. [Pietta, P.S. and Marshall, G.R., *Chem. Commun.*, 650 (1970)], and Orlowski et al., [*J. Org. Chem.*, 41, 3701 (1976)]. The cross-linked polystyrene BHA resin is available from chemical supply houses. The designation

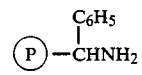

represents the BHA resin in which (P) is the polystyrene portion of the resin.

Alternatively, one can start from a resin which is an amino-methyl resin instead of a BHA resin.

The assembly of the resin-peptide from amino-methyl resin preferably includes a step in which a "handle" of the type described by Gaehde and Matsueda (Int. J. Peptide Protein Res. 18, 451–458 (1981)) is incorporated between the resin and the terminal amino acid of the polypeptide. More preferably, arginine or norleucine is incorporated between the resin and the "handle" as an internal reference standard.

Thus, BOC-Tosyl-Arg is reacted with the resin in the presence of dicyclohexylcarbonyldiimide (DCCI) and hydroxybenzotriazole (HOBT) to form

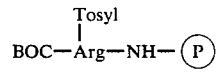

The BOC group is removed by adding acid to this product (such as HCl in dioxane or trifluoroacetic acid in toluene or in methylene chloride) and then neutralizing with e.g. diisopropylamine. Then the BOC-protected "handle",

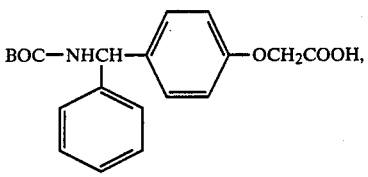

DCCI and HOBT are added to couple the BOC-handle to the deprotected arginine residue. Following removal of the BOC group from the handle, by acidification and neutralization, cycle 32 begins in which BOC-proline is coupled to the deprotected nitrogen of the "handle".

In general, each amino acid is reacted with the resin peptide in a suitable solvent such as toluene, chloroform, methylene chloride, or dimethyl formamide, in the presence of a coupling agent, and subsequently deprotected with acid followed by a neutralizing step; then the next amino acid is added, and so forth.

The amino acids are added one at a time to the insoluble resin until the total peptide sequence has been built up on the resin. The functional groups of the amino acids are protected by blocking groups. The α-amino group of the amino acids is protected by a tertiary butyloxycarbonyl group or an equivalent thereof. This α-tertiary butyloxycarbonyl group we designate as BOC. The hydroxyl functions of serine and threonine are protected by a benzyl or benzyl derivative group such as 4-methoxybenzyl, 4-methylbenzyl, 3,4-dimethylbenzyl, 4-chlorobenzyl, 2,6-dichlorobenzyl, 4-nitrobenzyl, benzhydryl or an equivalent thereof. We use the term Bzl to represent the benzyl or benzyl derivative group.

The hydroxyl function of tyrosine may be unprotected, may be protected by a benzyl or benzyl derivative group as described above, as a Bzl group, or may be protected by a benzyloxycarbonyl or a benzyloxycarbonyl derivative such as 2-chlorobenzyloxycarbonyl or 2-bromobenzyloxycarbonyl group or equivalent thereof. We use the term W to represent either no protective group, a Bzl group, a benzyloxycarbonyl group or a benzyloxycarbonyl derivative group.

The thiol function of cysteine may be protected by benzyl or benzyl derivative protective groups described above and designated Bzl, and preferably p-methylbenzyl or p-methoxybenzyl; or by an alkylthio group such as methylthio, ethylthio, n-propylthio, n-butylthio, t-butylthio or equivalents thereof. We use the character $R_2$ to represent an alkylthio group or Bzl, and the character $R_1$ to represent Bzl when $R_2$ is alkylthio and to represent alkylthio when $R_2$ is Bzl. Alternatively, $R_1$ may be another cysteine group and when this is the case $R_2$ is Bzl. The guanidine function of arginine may be protected by a nitro group, a tosyl group or an equivalent thereof. We use the character T to represent either a nitro group or a tosyl group. The ε-amino function of lysine may be protected preferably by FMOC (9-fluorenylmethyloxycarbonyl) or by a benzyloxycarbonyl group or a benzyloxycarbonyl derivative such as a 2-chlorobenzyloxycarbonyl, 3,4-dimethylbenzyloxycarbonyl, or equivalents thereof. We use the character V to represent these groups. The protective groups used on the imidazole nitrogen of histidine are tosyl, benzyloxymethyl, or benzyloxycarbonyl and are designated as V. The γ-carboxylic acid group of glutamic acid is protected by a benzyl or benzyl derivative group such as described for the protection hydroxyl function of serine and threonine. These protective groups are represented by the character Bzl.

The invention will be described herein with particular reference to the synthesis of human calcitonin.

As may be seen from the formula given above for human calcitonin, 32 amino acids are involved and in this formula the positions are numbered according to the accepted procedure beginning at position 1 for the Cys on one end of the chain, and ending with Pro at position 32 at the other end of the chain. For clarity of description, this same numbering system will be followed in referring to the cycles of the synthesis. The assembly of the amino acids of human calcitonin begins with cycle 32 which involves the coupling of proline and continues with cycle 31 which involves the coupling of alanine, etc.

Preferred amino acid reactants for use in each of the 32 cycles of the synthesis of human calcitonin (used for exemplification only) are given in the following Table I:

TABLE I

| Cycle Number | Amino Acid Reactant |
|---|---|
| 32 | BOC—L-proline |
| 31 | BOC—L-alanine |
| 30 | BOC—glycine |
| 29 | BOC—L-valine |
| 28 | BOC—glycine |
| 27 | BOC—L-isoleucine |
| 26 | BOC—L-alanine |
| 25 | BOC—O—benzyl-L-threonine |
| 24 | BOC—L-glutamine |
| 23 | BOC—L-proline |
| 22 | BOC—L-phenylalanine |
| 21 | BOC—O—benzyl-L-threonine |
| 20 | BOC—N(im)-CBZ-L-histidine |
| 19 | BOC—L-phenylalanine |
| 18 | BOC—ε-2-chlorobenzyloxycarbonyl-L-lysine or BOC—ε-9-fluorenylmethyloxycarbonyl-L-lysine |
| 17 | BOC—L-asparagine |
| 16 | BOC—L-phenylalanine |
| 15 | BOC—L-aspartic acid β-benzyl ester |
| 14 | BOC—L-glutamine |
| 13 | BOC—O—benzyl-L-threonine |
| 12 | BOC—O—bromo-benzyloxycarbonyl-L-tyrosine |
| 11 | BOC—O—benzyl-L-threonine |
| 10 | BOC—glycine |
| 9 | BOC—L-leucine |
| 8 | BOC—L-methionine |
| 7 | BOC—S—p-methylbenzyl-L-cysteine, or BOC—S—p-methoxybenzyl-L-cysteine |
| 6 | BOC—O—benzyl-L-threonine |
| 5 | BOC—O—benzyl-L-serine |
| 4 | BOC—L-leucine |
| 3 | BOC—L-asparagine |
| 2 | BOC—glycine |
| 1 | BOC—S—thioethyl-L-cysteine, or BOC—S—thio-t-butyl-L-cysteine |

The cysteines added in cycles 1 and 7 can alternatively be other S-n-alkyl thio derivatives with up to 6 carbon atoms.

Each of the amino acid derivatives mentioned in Table I may be purchased from supply houses. Typical satisfactory reactants for other calcitonins, oxytocin, somatostatin, and vasopressin, are disclosed in U.S. Pat. No. 4,212,795.

The following is an example of the preparation of a human calcitonin peptide which can subsequently be cyclized in accordance with the present invention. This example is not to be construed as limiting; the reader familiar with this subject will recognize that conditions, solvents, and procedures which produce equivalent results can be employed.

EXAMPLE 1

Neutralization of Amino-methyl resin

A 20.6 g sample of aminomethyl resin hydrochloride, corresponding to 20 mmoles amine groups (i.e. with a substitution of 0.973 milliequivalents of amine groups per gram of resin) was placed in the reaction vessel of a Vega Model 50 Peptide Synthesizer (Vega Biochemicals, Division of Vega Laboratories Inc., P.O. Box 11648, Tucson, Arizona 85734). The resin was swollen by shaking in methanol (300 ml) for five minutes and then was washed with methylene chloride (3×150 ml, 1 minute each). It was treated twice with 5% di-isopropylamine (DIA) in methylene chloride (200 ml each, once for 1 minute and a second time for 2 minutes. It was washed once with methylene chloride (150 ml, 1 minute) then retreated with 5% DIA in methylene chloride (200 ml, 1 minute) and washed again thrice with methylene chloride (150 ml, 1 minute each) and thrice with dimethyl formamide (150 ml, 1 minute each).

Introduction of Arginine as Internal Reference Amino-acid (IRA)

To the neutralized resin, containing 20 mmoles amino groups was added the acylating solution containing 50 mmoles N($\alpha$)BOC, N(G)-Tosyl-L-Arginine. This acylating solution was prepared by dissolving BOC(Tos)Arg (25.7 g, 60 mmoles) and 1-hydroxybenzotriazole hydrate (10.7 g, 70 mmoles) in dimethyl formamide (200 ml). The resulting solution was cooled to 0°-5° C. and 2M N,N'-dicyclohexylcarbodiimide solution in toluene (30 ml, 60 mmoles) was added. After stirring at room temperature for thirty minutes, the precipitate of dicyclohexylurea was filtered off and the filtrate was added to the resin.

The mixture was shaken overnight for convenience, although a coupling time as short as one hour would be adequate. The resin was drained and washed for one minute each time with three 150 ml portions of DMF, three 150 ml portions of methanol and six 150 ml portions of methylene chloride. A ninhydrin test [Kaiser et al, Anal. Biochem. 34, 595-8 (1969)] was performed and on all occasions was found to be negative. If it should have been even slightly positive, recoupling would have been performed.

Removal of $\alpha$-BOC group

This was performed in one of two ways:

(a) Using 4 N HCl(g) in dioxane, preferably in the presence of 2% v/v 2-mercaptoethanol.

The resin from above was treated as follows:

| | | |
|---|---|---|
| Dioxane 2% v/v 2-mercaptoethanol | 3 × 150 ml | 1 minute each |
| 3.5-4.0 N HCl in dioxane + 2% v/v 2-mercaptoethanol | 2 × 200 ml | 1 × 1 minute, 1 × 30 minutes |
| Dioxane + 2% v/v 2-mercaptoethanol | 3 × 150 ml | 1 minute each |
| Methanol | 3 × 150 ml | 1 minute each |
| Methylene Chloride | 3 × 150 ml | 1 minute each |
| Di-isopropylamine (5% v/v) in methylene chloride | 2 × 200 ml | 1 × 1 minute, 1 × 2 minutes |
| Methylene Chloride | 3 × 150 ml | 1 minute each |
| DIA (5% v/v) in methylene chloride | 1 × 200 ml | 1 minute |
| Methylene Chloride | 3 × 150 ml | 1 minute each |
| DMF | 3 × 150 ml | 1 minute each |

(b) Using 50% V/V trifluoroacetic acid in methylene chloride, preferably in the presence of 2% V/V 2-mercaptoethanol.

The BOC-protected resin is treated as follows:

| | | |
|---|---|---|
| Methylene chloride + 2% v/v 2-mercaptoethanol | 3 × 150 ml | 1 minute |
| 50% v/v TFA in methylene chloride + 2% v/v 2-mercaptoethanol | 2 × 200 ml | 1 × 1 min., 1 × 30 min. |
| Methylene chloride + 2% v/v 2-mercaptoethanol | 3 × 150 ml | 1 minute |
| Methanol (15% v/v) in methylene chloride | 3 × 150 ml | 1 minute |
| Methylene Chloride | 1 × 150 ml | 1 minute |
| Di-isopropylamine (5% v/v) in methylene chloride | 2 × 200 ml | 1 × 1 min., 1 × 2 min. |
| Methylene Chloride | 1 × 150 ml | 1 minute |
| Di-isopropylamine (5% v/v) in methylene chloride | 1 × 200 ml | 1 minute |
| Methylene Chloride | 3 × 150 ml | 1 minute |
| DMF | 3 × 150 ml | 1 minute |

Addition of N-BOC-p-($\alpha$-aminophenylmethyl)phenoxyacetic acid

This was carried out as described for the arginine IRA except that only a two-fold excess, 40 mmoles, of acylating solution was utilized.

Removal of the BOC group was performed exactly as for the Arg IRA.

Addition of Pro 32, Ala 31, Gly 30, Val 29, Gly 28, Ile 27, Ala 26, Thr 25, Glu 24, Pro 23, Phe 22, Thr 21

In general, each of these residues was incorporated as described for the Arg IRA and the BOC groups were removed similarly using either HCl/dioxane or TFA.

Completeness of coupling of Ala (31) to Pro (32) and of Phe (22) to Pro (23) was monitored by the isatin test (Kaiser E., Bossinger C.D., Colescott, R.L. and Olsen, D.B., Analytica Chimica Acta., 118, 149 (1980)).

Also Gly (28) and Ile (27) may be incorporated together as using the dipeptide BOC Ile Gly under identical conditions to those for the individual amino-acids. The only advantage is to reduce the synthesis time.

In addition, it is preferred that Pro (23) and Phe (22) be incorporated using the dipeptide BOC Phe Pro, using the same conditions as for the individual amino-acids.

Addition of His (20)

The acylating solution was prepared in the same way as for the Arg IRA but, after adding the solution of DCCI in toluene, the cold solution was added immediately to the resin.

Addition of Phe (19)

Same as for Arg IRA.

Addition of Lys (18) using $\epsilon$-2-chlorobenzyloxycarbonyl-L-lysine:

Acylating solutions are prepared as described for the Arg IRA. The preferred method for deblocking is to use TFA rather than HCl from Lys (18) down to the end. After Met (8) is added, it is essential that 2-mercaptoethanol be present during acid deblocking treatments.

Addition of Lys (18) using ε-FMOC and all other residues

Acylating solutions are prepared as described for the Arg IRA but dimethyl acetamide is preferred as solvent over DMF. Also, all DMF washes were replaced by dimethylamine washes.

The preferred method for deblocking is to use TFA and for neutralization, all di-isopropylamine in methylene chloride treatments were replaced by 5% v/v triethylamine in methylene chloride treatments, and each of these were for only ten seconds.

After incorporation of Cys (1), the BOC group is not removed with TFA but is left on, to be removed during the HF cleavage. If 2-chlorobenzyloxycarbonyl is used on Lys, HF cleavage is the next step. If FMOC is used, this must be removed before HF cleavage, for instance using this procedure:

Treat the resin as follows:
wash with DMF 3×1 min.×150 ml
10% Piperidine in DMF 1×1 min., 1×15 min. 200 ml each
DMF 3×1 min.×150 ml
$CH_2Cl_2$ 6×1 min.×150 ml Resin Peptide Cleavage The peptide is cleaved from the resin peptide resulting from cycle 1 by treatment with liquid hydrogen fluoride (HF). The HF cleavage reaction may be performed by treating a mixture of the resin peptide in a mixture of m-cresol and ethanedithiol (ratio of 1:1 to 1:2), or in anisole (0.5 to 5 ml. for each gram of resin peptide) with liquid HF (2 to 20 ml. for each gram of resin peptide) for 0.5 to 20 hours at −20 degrees to +15 degrees centigrade, preferably at 0° C. After the reaction period, the excess HF may be removed by evaporation and the resulting mixture of peptide and resin beads may be extracted with organic solvent such as ethyl acetate, diethyl ether, toluene or the like to remove the m-cresol/ethanedithiol or anisole and residual HF. The peptide may be separated from the resin beads by extraction into aqueous acetic acid or may be stored as a mixture of resin plus crude peptide. The peptide at this stage is not cyclic but is the non-cyclic product without the disulfide bond between the cysteines at positions 1 and 7 in the molecule.

The HF treatment removes all blocking groups from the peptide, except the S-alkylthio blocking groups on the thiol function of cysteine residue at position 1. The S-alkylthio-L-cysteine residue is stable to the HF cleavage procedure and remains intact throughout the cleavage and extraction procedures. The S-paramethoxybenzyl (or para-methylbenzyl)-L-cysteine residue is cleaved by HF to yield a cysteine residue with a free thiol function.

Thus, the peptides obtained after HF cleavage would be represented by the formula:

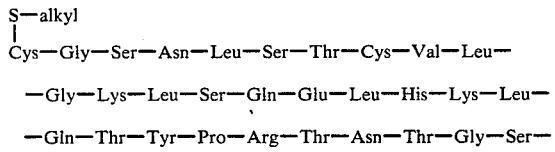

—Gln—Thr—Tyr—Pro—Arg—Thr—Asn—Thr—Gly—Ser—

—Gly—Thr—Pro—$NH_2$

Preferably, the peptide is 1-S-thioethyl-substituted.

In one embodiment of the present invention, the peptide starting with resin plus cleaved crude peptide is cyclized by first stirring with distilled water using 600 ml water per gram of resin plus peptide mixture, i.e. 1.67 mg resin plus peptide per ml water, for 15–60 minutes, representing a nominal final concentration of 0.4 to 1.8, and preferably 0.7 to 1.0, milligrams of peptide per ml of solution. The pH of this solution is then adjusted to a value in the range 8.5 to 9.0, and preferably but not over about 9.0, for instance and preferably by the addition of ammonium hydroxide solution. The mixture is stirred in a container under a stream of an inert gas such as nitrogen or under air for about 4 to 24 hours. Monitoring by HPLC indicates that about 4 hours is all that is needed but leaving overnight frequently is convenient and HPLC indicates that this does not harm the peptide. The conditions should not be so oxidizing that side reactions occur such as sulfoxide formation at methionine (8). The reaction period can be stopped when the effluent gas stream no longer contains alkylmercaptan. All insoluble material is removed by filtration or centrifugation.

For example, 5.8 g resin plus peptide were added to 3500 ml distilled water, stirred for one hour and filtered. The pH of the solution was 3.78. The pH was adjusted by 8.84 by dropwise addition of $NH_4OH$ solution and cyclization was allowed to proceed overnight under nitrogen. Next day, the mixture was centrifuged and the centrifugate lyophilized to give 2.35 g crude hCT. Centrifugation removed a substantial amount of peptide by-products. HPLC indicated that these are principally high molecular weight impurities and no hCT was present. Alternatively, after centrifugation, the pH of the centrifugate may be lowered to about 3.5–5.5 by the addition of glacial acetic acid.

The crude peptide solutions at pH 5.0 from the above synthesis may be concentrated using an ion-exchange procedure. The concentrate or lyophilizate after redissolving, may be purified by a combination of gel-filtration procedures, ion-exchange chromatography methods and partition chromatography. The final purified product may be obtained from solution by freeze-drying as a fluffy white solid. The product gives the correct amino acid analysis for the desired peptide.

The following is an example of the purification of the peptide that has been cyclized in this manner:

2.35 g of crude hCT from the above synthesis (at approximately 200 ml) was dissolved in 0.2M acetic acid and was purified by ion-exchange chromatography using a Whatman CM-52 column eluted with an acetic acid gradient (0.2–1.0M). The pH must be below 7 and preferably from 1 to 3. The calcitonin fractions from this column were pooled and lyophilized to afford 566 mg of peptide which, by HPLC, contain 350 mg hCT, and then purified further by HPLC on a duPont "Zorbax $C_{18}$" reverse-phase octadecyl silica gel column eluted with a gradient of 10–40% ethanol in 2M aqueous acetic acid whose condictivity was adjusted to 10 milliSiemens with ammonium hydroxide solution. The fractions containing hCT were pooled based on analytical HPLC profiles and ethanol removed using a rotary evaporator. The residual liquid was lyophilized. The resulting powder was redissolved in 0.5 N aqueous acetic acid plus a few drops of 50% acetic acid to ensure complete dissolution and was desalted with a Sephadex G-25 (fine) gel-filtration column and eluted with 0.5 N aqueous acetic acid.

In an alternative embodiment, the uncyclized resin following cleavage from the resin is extracted with 0.1N aqueous acetic acid and subjected to the ion-exchange chromatography set forth above using a CM-52 column. The product is an enriched solution of S-alkyl, e.g., 1-S-thioethyl, dihydro-human calcitonin which can be recovered by lyophilization. This product in its solid form is believed to be novel, as it could not be recovered from solution by previously known procedures without cyclization. The purified intermediate can be redissolved in water or 0.1 N acetic acid and cyclized within 10-30 minutes as taught above to provide human calcitonin.

To illustrate the advantage of cyclizing the cleaved peptide within the ranges of pH and concentration which constitute the invention, the following table presents the yields of cyclization operations carried out on identical starting samples of uncyclized 1-S-ethylthio human calcitonin under identical conditions except at various concentrations and yields. The cyclizations were allowed to proceed overnight (20 hours) under nitrogen at pH 9.0.

The results were:

| Run | pH | Concentration (mg resin + peptide)/(ml water) | Yield mg hCT |
|---|---|---|---|
| A | 9.0 | 0.19 | 10.7 |
| B | 9.0 | 0.56 | 12.8 |
| C | 9.0 | 1.67 | 25.3 |
| D | 9.0 | 5.0 | 2.4 |

The process of the present invention provides a yield which is higher, to an unexpected degree, than the conditions outside those set forth in the following claims. In addition, cyclization under the claimed conditions proceeds with rapidity, generally in less than about 10 minutes.

While only certain embodiments of our invention have been described in specific detail it will be apparent to those skilled in this art that many other specific embodiments may be practiced and many changes may be made, all within the spirit of the invention and the scope of the appended claims.

The following table presents the yields of cyclization operations carried out on identical starting samples of uncyclized 1-S-ethylthio dihydro-human calcitonin under identical concentration conditions (1.67 mg resin+peptide/ml water). The starting samples, however, were not identical to those in the previous table. Cyclization was allowed to proceed overnight (20 hours).

| Run | pH | Yield (peak area in sq. cm.) |
|---|---|---|
| E | 8.0 | 4.80 |
| F | 9.0 | 6.55 |
| G | 10.0 | 4.80 |
| H | 11.0 | 2.84 |

Here, the yield figures are relative, representing the area of the hCT peak obtained by performing HPLC on 50 ul samples of E-H after 20 hours. It is nonetheless apparent that the yield obtained by cyclizing at pH=9.0 was over 35% higher than the yield obtained at pH=8.0 or pH=10.0.

What is claimed is:

1. A process for forming a disulfide bridge in a peptide containing at least one pair of cysteine moieties which are initially uncyclized, comprising maintaining a solution of the peptide at a pH above 8.5 but not exceeding 9.0, until the cyclization has taken place.

2. A process for forming a disulfide bridge in a peptide containing at least one pair of cysteine moieties which are initially uncyclized,
wherein
one of the cysteine moieties of the initially uncyclized peptide is a residue substituted with an alkyl group containing up to 6 carton atoms,
the concentration of the initially uncyclized peptide is 0.7 to 1.0 mg of peptide per ml of solution, and
the solution of peptide is maintained at a ph above 8.5 but not exceeding 9.0, until the cyclization has taken place.

3. The process of claim 2 wherein the peptide is a calcitonin having the structure of a naturally occurring calcitonin, or a deletion, substitution, or addition analog thereof.

4. the process of claim 2 wherein the calcitonin is human calcitonin or an analog thereof.

* * * * *